(12) United States Patent
Kuo et al.

(10) Patent No.: US 8,428,334 B2
(45) Date of Patent: Apr. 23, 2013

(54) INSPECTION SYSTEM

(75) Inventors: Cooper S. K. Kuo, Taipei (TW); Ron Tsai, Taipei (TW)

(73) Assignee: Cooper S.K. Kuo, Wen Shan (TW)

( * ) Notice: Subject to any disclaimer, the term of this patent is extended or adjusted under 35 U.S.C. 154(b) by 503 days.

(21) Appl. No.: 12/732,586

(22) Filed: Mar. 26, 2010

(65) Prior Publication Data

US 2011/0235868 A1 Sep. 29, 2011

(51) Int. Cl.
*G06K 9/00* (2006.01)

(52) U.S. Cl.
USPC ........... 382/141; 382/169; 382/172; 382/222; 382/205

(58) Field of Classification Search .......... 382/141–152, 382/169, 170, 172, 205, 217–222
See application file for complete search history.

(56) References Cited

U.S. PATENT DOCUMENTS

| | | | |
|---|---|---|---|
| 5,553,158 A | 9/1996 | Bittar | |
| 5,717,780 A | 2/1998 | Mitsumune et al. | |
| 6,178,257 B1 | 1/2001 | Alumot et al. | |
| 6,360,005 B1 | 3/2002 | Aloni et al. | |
| 7,379,580 B2 | 5/2008 | Levin et al. | |
| 7,643,668 B2 * | 1/2010 | Nakatani | 382/168 |
| 2002/0154307 A1 | 10/2002 | Bjork | |
| 2006/0044425 A1 | 3/2006 | Yeung et al. | |
| 2006/0233434 A1 * | 10/2006 | Hamamatsu et al. | 382/149 |

FOREIGN PATENT DOCUMENTS

| | | |
|---|---|---|
| CN | 1103978 A | 6/1995 |
| CN | 1610826 A | 4/2005 |
| CN | 101556250 A | 10/2009 |
| EP | 0 514 301 A1 | 11/1992 |
| JP | 2001-165865 A | 6/2001 |
| JP | 2002-250698 | 9/2002 |
| JP | 2004-028836 A | 1/2004 |
| JP | 2004-534949 A | 11/2004 |
| JP | 2005-510709 A | 4/2005 |
| JP | 2006-266752 | 10/2006 |
| JP | 2006-292503 A | 10/2006 |
| JP | 2008-082999 A | 4/2008 |
| KR | 10-0150689 | 10/1998 |
| KR | 2003-0089542 | 11/2003 |

OTHER PUBLICATIONS

Notice of Submission of Opinion for Korean Patent Application No. 10-2010-0051106, mailed Jul. 18, 2011.

(Continued)

*Primary Examiner* — Gregory J Toatley
*Assistant Examiner* — Iyabo S Alli
(74) *Attorney, Agent, or Firm* — Alston & Bird LLP

(57) ABSTRACT

A system for inspecting a product that includes a scanner to scan across the product and generate an image of the product, the image including a matrix of pixels each having a grayscale value, and an analyzing device electrically coupled with the scanner to receive and analyze the image of the product, the analyzing device including a microprocessor to calculate a reference grayscale value associated with each of the pixels in the image, wherein the reference grayscale value includes an average of the grayscale values of pixels located adjacent to the each pixel, a memory to store the reference grayscale value associated with each of the pixels and at least one threshold associated with the reference grayscale value, and a comparing module to compare the grayscale value of each of the pixels in the image with the at least one threshold associated with the each pixel.

20 Claims, 8 Drawing Sheets

OTHER PUBLICATIONS

Extended European Search Report for European Patent Application No. 10165454.9, mailed Jun. 1, 2011.
Office Action mailed Jan. 27, 2012 in corresponding Korean Patent Application No. 10-2010-0051106.
Abstract of Kean Patent Publication No. 2003-0089542 is attached.

Japan Application No. 2010-168602, First Office Action dated Feb. 28, 2012.
Chinese Application No. 2010-168602, First Office Action dated Aug. 24, 2012.

* cited by examiner

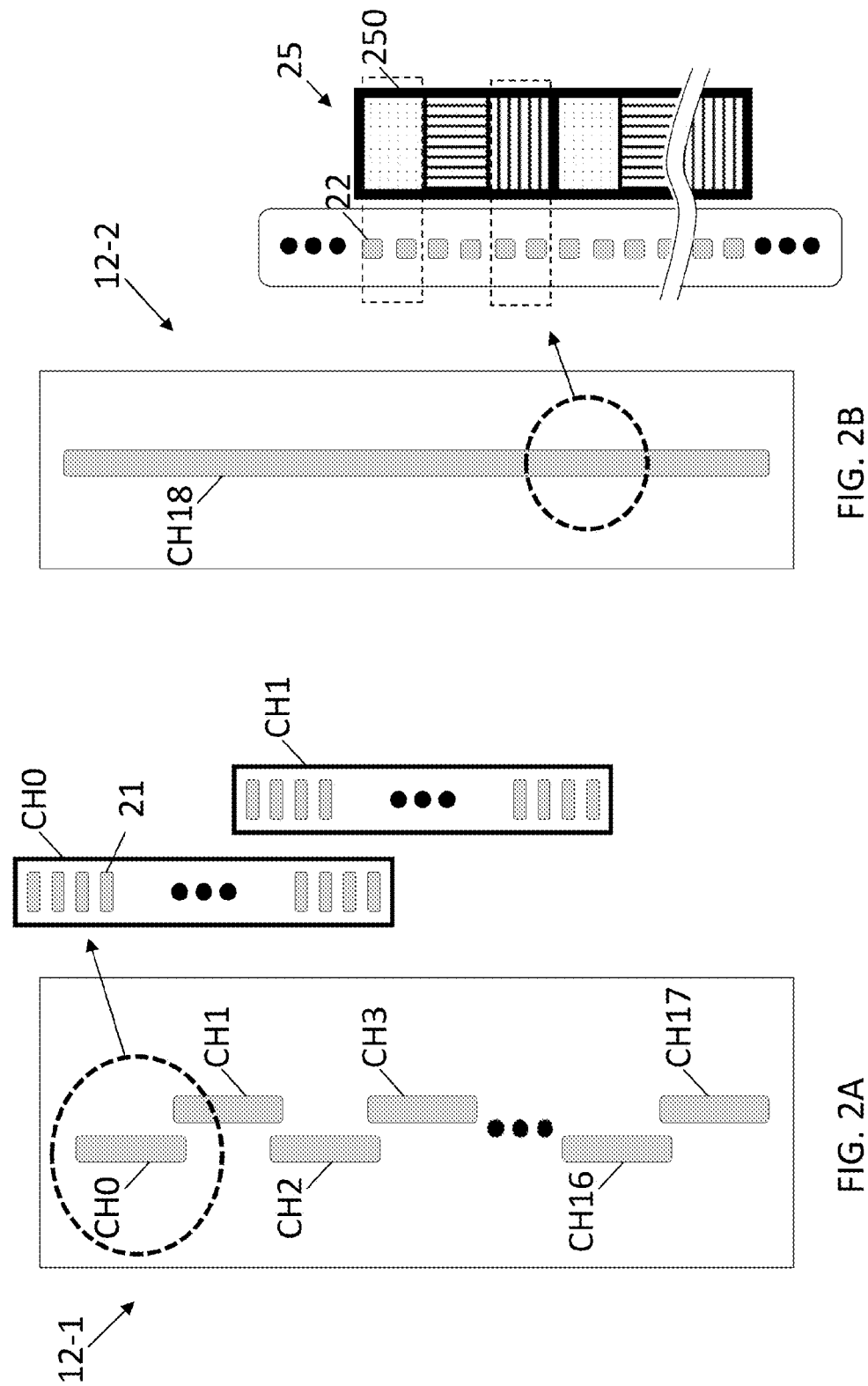

INSPECTION SYSTEM

BACKGROUND OF THE INVENTION

The invention generates relates to optical inspection and, more particularly, to a system for inspecting defects or features of an object of interest using a scanner.

Display devices such as liquid crystal display (LCD) devices are used for electronically displaying information including text, images and moving pictures. An LCD may include a number of layers such as polarized filter, glass substrate, color filter, liquid crystal and reflective surface, which may determine the quality of the LCD. To examine whether an LCD is a qualified one, that is, whether the LCD has defects less than a predetermined amount, human eye inspection may sometimes be employed. However, eye inspection may mean time-consuming, laborious and imprecise in the mass-production of LCDs. Moreover, with the advance in semiconductor manufacturing, it may become more difficult to examine LCD products with down-sized features by human eye inspection.

It may therefore be desirable to have an inspection system that is able to automatically inspect defects or features of an object, for example, a layer of interest in an LCD device.

BRIEF SUMMARY OF THE INVENTION

Examples of the present invention may provide a system for inspecting a product. The system may include a scanner to scan across the product and generate an image of the product, the image including a matrix of pixels each having a grayscale value, and an analyzing device electrically coupled with the scanner to receive and analyze the image of the product, the analyzing device including a microprocessor to calculate a reference grayscale value associated with each of the pixels in the image, wherein the reference grayscale value includes an average of the grayscale values of pixels located adjacent to the each pixel, a memory to store the reference grayscale value associated with each of the pixels and at least one threshold associated with the reference grayscale value, and a comparing module to compare the grayscale value of each of the pixels in the image with the at least one threshold associated with the each pixel.

Some example of the present invention may also provide a system for inspecting a product. The system may include a scanner including a number of scanning units arranged in a first direction and configured to scan across the product in a second direction orthogonal to the first direction, the scanner generating an image of the product, the image including a matrix of pixels each having a grayscale value, a microprocessor to calculate a reference grayscale value associated with each of the pixels in the image, wherein the reference grayscale value includes an average of the grayscale values of pixels located adjacent to the each pixel, and a comparing module to compare the grayscale value of each of the pixels in the image with a first threshold and a second threshold associated with the each pixel, wherein the first threshold includes an upper limit of the reference grayscale value and the second threshold includes a lower limit of the reference grayscale value.

Examples of the present invention may still provide a system for inspecting a product. The system may include a first scanner to scan across the product and generate a first image of the product, the first image including a matrix of pixels each having a grayscale value, a second scanner to scan across the product and generate a second image of the product, the second image including a matrix of pixels each having a grayscale value, and an analyzing device electrically coupled with the scanner to receive and analyze the first and second images of the product, the analyzing device including a microprocessor to calculate a reference grayscale value associated with each of the pixels in the first and second images, wherein the reference grayscale value includes an average of the grayscale values of pixels located adjacent to the each pixel, a memory to store the reference grayscale value associated with each of the pixels in the first and second images and at least one threshold associated with the reference grayscale value, and a comparing module to compare the grayscale value of each of the pixels in the first and second images with the at least one threshold associated with the each pixel.

Additional features and advantages of the present invention will be set forth in portion in the description which follows, and in portion will be obvious from the description, or may be learned by practice of the invention. The features and advantages of the invention will be realized and attained by means of the elements and combinations particularly pointed out in the appended claims.

It is to be understood that both the foregoing general description and the following detailed description are exemplary and explanatory only and are not restrictive of the invention as claimed.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, examples are shown in the drawings. It should be understood, however, that the invention is not limited to the precise arrangements and instrumentalities shown in the examples.

In the drawings:

FIG. 2A is a schematic diagram of a scanner adapted to use in the system illustrated in FIG. 1A in accordance with an example of the present invention;

FIG. 2B is a schematic diagram of a scanner adapted to use in the system illustrated in FIG. 1A in accordance with another example of the present invention;

DETAILED DESCRIPTION OF THE INVENTION

Reference will now be made in detail to the present examples of the invention, examples of which are illustrated in the accompanying drawings. Wherever possible, the same reference numbers will be used throughout the drawings to refer to the same or like parts.

Figure 1A:
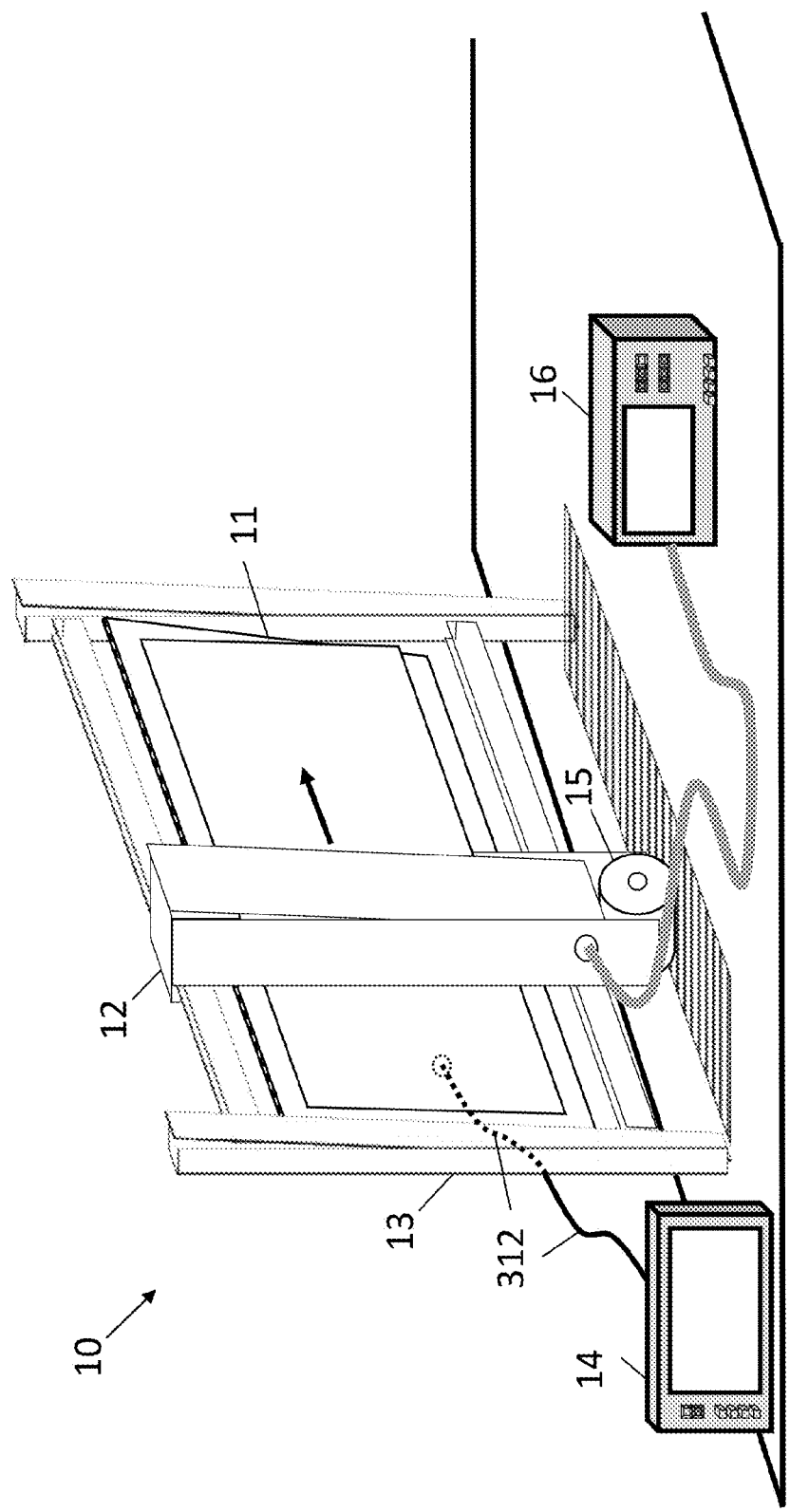
FIG. 1A is a diagram of a system for inspection in accordance with an example of the present invention.

FIG. 1A is a diagram of a system 10 for inspection in accordance with an example of the present invention. Referring to FIG. 1A, the system 10 may include a product under inspection such as a panel 11, a scanner 12, a signal generator 14 and an analyzing device 16.

The panel 11 to be inspected may be placed in a support frame 13. Furthermore, the panel 11 may include but is not limited to a display panel such as a liquid crystal display (LCD) panel that may include one or more layer such as polarized filters, a glass substrate, a color filter and a liquid crystal layer. Due to manufacturing factors, the panel 11 may include in at least one of the layer one or more defect such as scratch, crack, bubble, void and dust.

The scanner 12 may be configured to move with respect to the panel 11 at a predetermined speed when driven by a motor 15. Specifically, the scanner 12 may include a number of sensor cells arranged in a first direction, for example, a column direction, which may scan across the panel 11 as the scanner 12 moves in a second direction, for example, a row direction, as indicated by an arrow. Moreover, the distance between the scanner 12 and the panel 11 may be adjusted by a robot arm (not shown) so as to facilitate the inspection of a layer of interest in the panel 11.

The scanner 12 may provide data to the analyzing device 16 after scanning the panel 11. The data may include an image of the panel 11 in a matrix of pixels. Accordingly, the image may provide information on the location or coordinates of each of the pixels. Furthermore, each of the pixels carries intensity information corresponding to an amount or quantity of light. Specifically, each pixel has a grayscale value that may range from, for example, 0 to 255, where "0" represents black and "255" represents white.

The signal generator 14, electrically coupled with the panel 11, may be used to generate a desired pattern for display on the panel 11. Based on the pattern, the panel 11 may generate a video frame of a specific color for inspection. The pattern in one example may include but is not limited to one of color red, green, blue, gray, white and black. For example, a video frame of color black may facilitate the detection of bright dots in the panel 11. As an alternative, a video frame of color white may facilitate the detection of dark dots in the panel 11. Moreover, a video frame of color gray may facilitate the detection of bright and dark dots in the panel 11.

The analyzing device 16 may include, for example, a computing device such as a personal computer or a workstation computer. The analyzing device 16 may be electrically coupled with the scanner 12 and configured to analyze the scanned data sent from the scanner 12. A report on the inspection result may be provided by the analyzing device 16. The report may include but is not limited to the number of defects, if any, in the panel 11, the type of defect such as scratch, crack, void or alien impurity, and the location or coordinates of the defects.

In operation, prior to inspection, an initializing process may be performed to calibrate system parameters, which may include display patterns, the sensitivity of a scanner and the distance between the scanner and a product under inspection. In the initializing stage, a sample of the products to be inspected may be provided. The sample product may include a multi-layer product or a single-layer product. In one example, the multi-layer product may include a display panel such as the panel 11, a touch panel, a wafer and a printed circuit board (PCB), and the single-layer product may include a glass layer, a color filter, a diamond and contact lenses.

The signal generator 16 may generate a desired pattern if the sample product is a display panel. In that case, a light module such as a backlight module of an LCD panel may be turned on. The scanner 12 may then be adjusted by a robot arm so as to ensure that a layer of interest in the sample product in focus. In one example according to the present invention, the focus distance of the scanner 12 may be approximately 15±1 millimeter (mm). That is, the scanner 12 may be designed with a near focus of approximately 14 mm and a far focus of approximately 16 mm. Furthermore, given a semiconductor-manufactured product, each layer therein may have a thickness of approximately 2 mm. Accordingly, by adjusting the distance between the scanner 12 and the product, a specific layer may be inspected.

Moreover, in the calibration stage, a first threshold and a second threshold associated with each sensor cell of the scanner 12 for the inspection may be determined. Due to manufacturing factors, a pixel having a grayscale value of, for example, 128 in the sample product may have different values when read by different sensor cells of the scanner 12. For example, a first cell may read a value of 148 while a second sensor cell may read 108. Although the sensitivity of the sensor cells of the scanner 12 may not be uniform, each sensor cell, which may be responsible for the scanning of a row of pixels, has a consistent offset in its scanning sensitivity. As a result, a defective pixel may be defected if its grayscale value is significantly different from an average grayscale value of its neighboring pixels when scanned by a same sensor cell. Accordingly, for example, the first sensor cell may have a first threshold of $BGV_1+10\%$ and a second threshold of $BGV_1-20\%$, wherein "BGV" refers to a "background grayscale value" or a reference value, which is an average grayscale value of pixels in the neighborhood of a pixel at issue. Furthermore, the sensor cell may have a first threshold of $BGV_2+10\%$ and a second threshold of $BGV_2-20\%$, wherein $BGV_2$ may be different from $BGV_1$. The reference values BGV of each sensor cell may be different from pixel to pixel because the panel 11 may not be uniform in display sensitivity, also due to manufacturing factors.

The number of neighboring pixels and the calculation of the reference value may depend on quality requirement. In one example, four or five adjacent pixels may be selected and their grayscale values may be averaged with a same weight. In another example, six or seven adjacent pixels may be selected and their grayscale values may be averaged with different weights. Consequently, taking the first sensor as an example, a first pixel having a grayscale value greater than 10% of the reference grayscale value associated with its neighboring pixels, the first pixel may be recognized as a bright dot. Moreover, a second pixel having a grayscale value smaller than 20% of the reference grayscale value associated with its neighboring pixels, the second pixel may be recognized as a dark dot. The range between the upper limit (+10%) and the lower limit (−20%) may also depend on quality requirement. The calibrated system parameters and the thresholds and reference grayscale values associated with each sensor cell for each pixel in the sample product may be stored in the analyzing device 16.

Next, a number of the products may be scanned by the scanner 12 one after another. An image of each of the products, including the grayscale values and the coordinates of the pixels, may be sent to the analyzing device 16 and stored therein. The analyzing device 16 may compare the grayscale value of each pixel with a reference grayscale value of the each pixel and determine whether the grayscale value is greater than a first threshold or smaller than a second threshold. Specifically, a pixel having a grayscale value significantly different from a reference grayscale value of its neighboring pixels may be identified.

The number of defects in each of the products may be calculated in the analyzing device 16. Furthermore, in one example according to the present invention, the analyzing device 16 may be configured to sort the products by the number of defects. For example, depending on the size and quality requirement, grade-A products may refer to those having less than, for instance, three defects, and grade-B products may refer to those having more than four defects. Moreover, the location or coordinates of the defects, if any, in each of the products may be provided by the analyzing device 16.

Figure 1B:
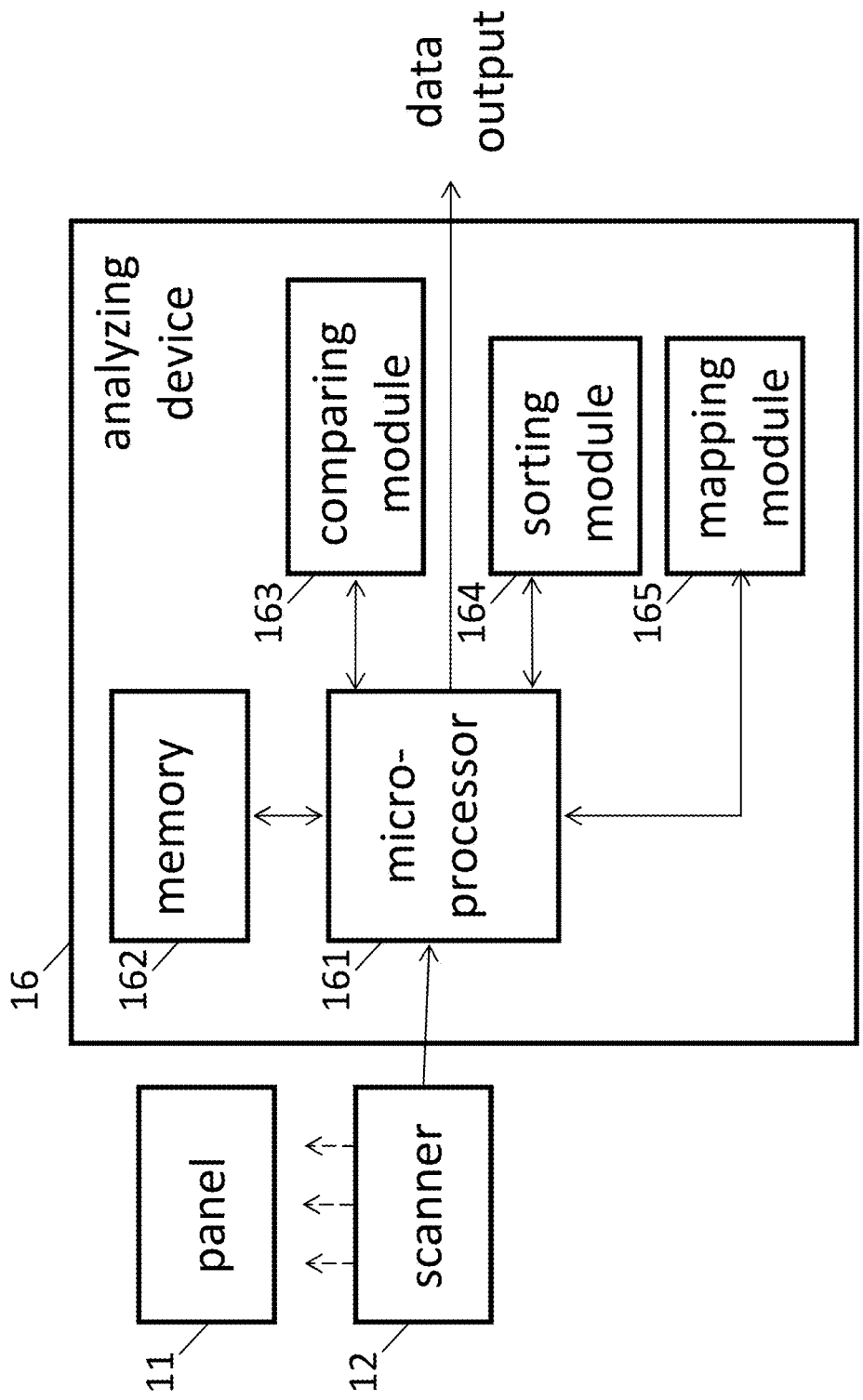
FIG. 1B is a block diagram of an analyzing device illustrated in FIG. 1A in accordance with an example of the present invention.

FIG. 1B is a block diagram of the analyzing device 16 illustrated in FIG. 1A in accordance with an example of the present invention. Referring to FIG. 1B, the analyzing device 16 may include a microprocessor 161, a memory 162, a comparing module 163, a sorting module 164 and a mapping module 165. The microprocessor 161 may receive from the scanner 12 image data, including a sample image of a sample product and a scanned image of an inspected product, and coordinate the operation of the comparing module 163, sorting module 164 and mapping module 165. Furthermore, the microprocessor 161 may calculate a reference grayscale value for each of pixels in an image. The memory 162 may be used to store the calibrated data, reference grayscale values, thresholds, sample image and scanned images. The comparing module 163 may be configured to compare pixels with the thresholds in grayscale value so as to identify defected pixels. The number of defects in each of the products may be calculated in, for example, the microprocessor 161. The sorting module 164 may be configured to sort the products by the number of defects. The mapping module 165 may be configured to map the defects, if any, in a coordinate system. The microprocessor 161 may provide a report on the number of defects in each of the products, the grade or quality of each of the products, the location of each of the defects, if any, in each of the products and the type of defect.

Skilled persons in the art will understand that the comparing module 163, sorting module 164 and mapping module 165 may be implemented in hardware or software, in which the former may be more advantageous in terms of operation speed while the latter may be more cost effective in terms of design complexity.

FIG. 2A is a schematic diagram of a scanner 12-1 adapted to use in the system 10 illustrated in FIG. 1A in accordance with an example of the present invention. Referring to FIG. 2A, the scanner 12-1 may include a number of scanning units or scanning channels "CH0" to "CH17" arranged in a first and a second columns. The first and second columns of scanning units may be staggered with respect to each other. Furthermore, each of the scanning units CH0 to CH17 may include a number of sensor cells 21. The sensor cells 21 may each include one of a charge coupled device (CCD) sensor or a complementary metal-oxide-semiconductor (CMOS) sensor. To avoid any gap between adjacent scanning units in different columns, for example, CH0 and CH1, the immediately adjacent scanning units CH0 and CH1 may overlap each other by a predetermined number of sensor cells, for example, six sensor cells. Similarly, the adjacent scanning units CH1 in the second column and CH2 in the first column may overlap each other by six sensor cells.

In one example according to the present invention, each of the scanning units CH0 to CH17 may include 344 sensor cells, and each of the sensor cells 21 may have a size of approximately 40 micrometer (um) by 40 um. The scanner 12-1 may thus provide a resolution of approximately 600 dots per inch (dpi). In another example, each of scanning units CH0 to CH17 may include 344 sensor cells 21 each having a size of approximately 10 um by 10 um. The scanner 12-1 may thus provide a resolution of approximately 2,400 dpi.

Skilled persons in the art will understand that the number of scanning units may increase or decrease to suit a practical application even though eighteen such scanning units CH0 to CH17 are used in the present example.

As previously discussed, during the calibration stage, each of the sensor cells of a scanner may be calibrated. Given the scanner 12-1 including 18 scanning units CH0 to CH17 each having 344 sensor cells 21, the calibrating process may be time consuming and a large memory may be required to store the reference grayscale values and thresholds associated with the sensor cells 21. However, the sensitivity of sensor cells in a same scanning unit may be substantially similar because they may be made in a same semiconductor manufacturing process. Accordingly, as an alternative, only the scanning units of a scanner are calibrated during the calibration stage.

FIG. 2B is a schematic diagram of a scanner 12-2 adapted to use in the system 10 illustrated in FIG. 1A in accordance with another example of the present invention. Referring to FIG. 2B, the scanner 12-2 may include a single scanning unit CH18. The scanning unit CH18 may include a number of sensor cells 22 arranged in a column, wherein at least two sensor cells 22 are responsible to scanning a sub-pixel 250 of a color filter 25. That is, the density of the sensor cells 22 of the scanner 12-2 may be at least twice that of the sub-pixels 250 of the color filter 25, which may avoid the "aliasing" effect that may occur in cameras.

Figure 3A:
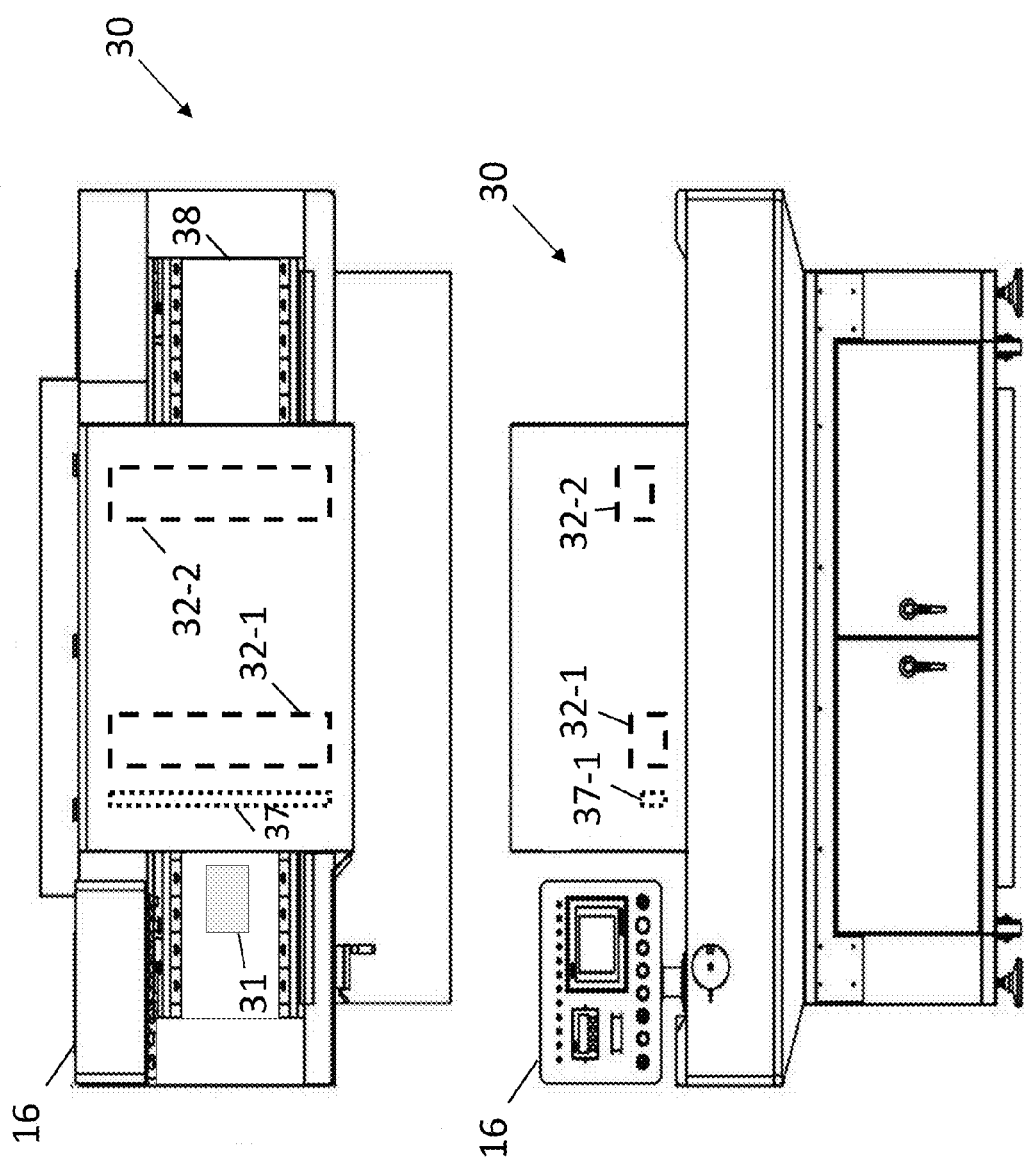
FIG. 3A is a diagram of a system for inspection in accordance with another example of the present invention.

FIG. 3A is a diagram of a system 30 for inspection in accordance with another example of the present invention, wherein the lower part is a front view and the upper part is a top view of the system 30. Referring to FIG. 3A, the system 30 may be similar to the system 10 described and illustrated with reference to FIG. 1A except that, for example, a conveyor belt 38 may replace the support frame 13. Specifically, products 31 to be inspected may be placed on the conveyor belt 38 and move with the conveyor belt 38. Accordingly, a continuous inspection of the products 31 may be achieved. The system 30 may include a first scanner 32-1, which may be immobilized with respect to the analyzing device 16, unlike the scanner 12 illustrated in FIG. 1A. Furthermore, the system 30 may also include a first light source 37-1 to facilitate inspection. In the present example, the first scanner 32-1 and the first light source 37-1 may be disposed at the same side of the product 31 under inspection.

The first scanner 32-1 may be disposed at a first distance from the product 31 and generate a first image associated with a first layer of interest in the product 31. Moreover, the system 30 may include a second scanner 32-2 disposed at the same side of the product 31 at a second distance from the product 31. The second scanner 32-2 may generate a second image associated with a second layer of interest in the product 31. The use of two or more scanners 32-1 and 32-2 may facilitate the identification of a defect in a specific layer of the product 31 by comparing the first and second images of the product 31. For example, if a bright dot is 12% greater than an associated upper threshold as scanned by the first scanner 32-1 and is 18% greater than an associated upper threshold as scanned by the second scanner 32-2, it may be determined that the bright dot is located in or near the second layer of the products 31. That is, an amount of offset from an upper limit or lower limit of a reference grayscale value may be compared by, for example, the comparing module 163 so as to identify the specific layer. Specifically, the comparing module 163 may be configured to compare a first amount of offset from the at least one threshold associated with a pixel in the first image with a second amount of offset from the at least one threshold associated with the pixel in the second image so as to determine a specific defective layer. The light intensity of the first light source 37-1, the first distance and second distance, may have been calibrated in the initialization stage.

Figure 3B:
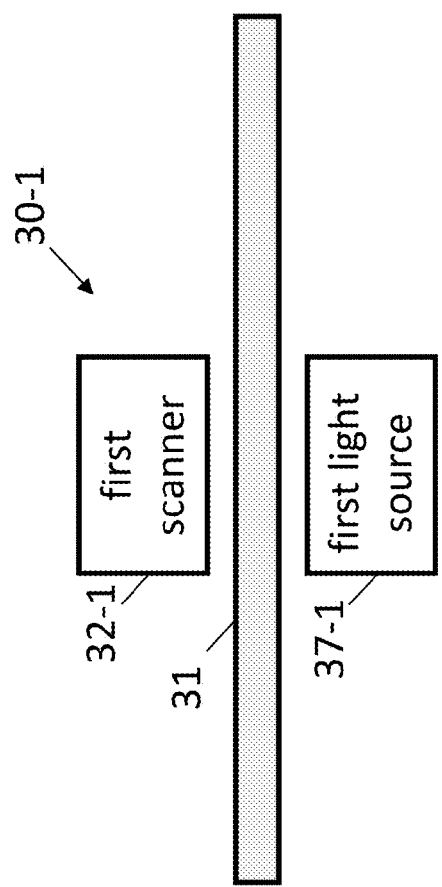
FIG. 3B is a schematic diagram of a system for inspection in accordance with yet another example of the present invention.

FIG. 3B is a schematic diagram of a system 30-1 for inspection in accordance with yet another example of the present invention. Referring to FIG. 3B, the first scanner 32-1 and the first light source 37-1 may be disposed at different sides of the product 31 under inspection. The product 31 in the present example may be optically transparent and may include one or more transparent layer.

Figure 3C:
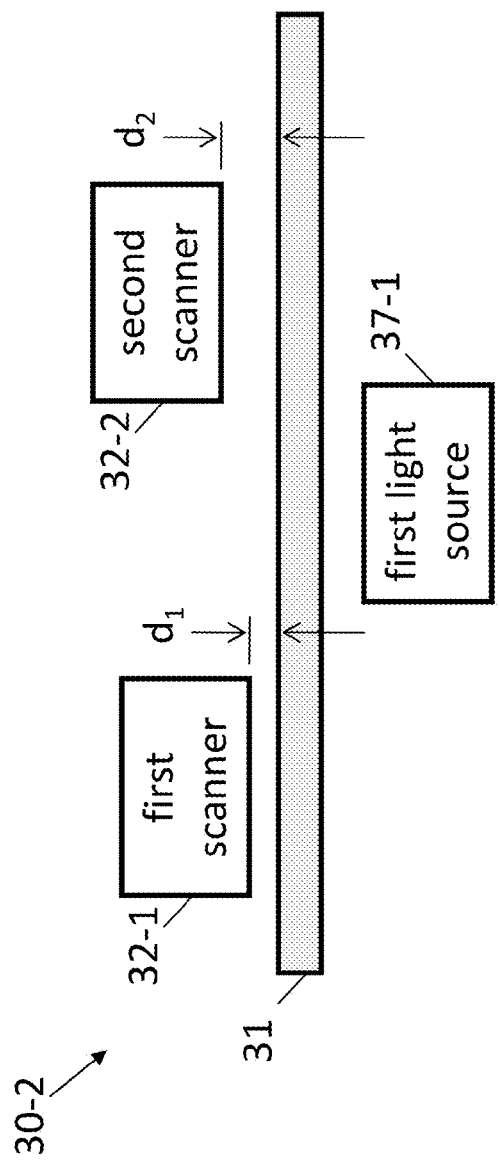
FIG. 3C is a schematic diagram of a system for inspection in accordance with still another example of the present invention.

FIG. 3C is a schematic diagram of a system 30-2 for inspection in accordance with still another example of the present invention. Referring to FIG. 3C, the system 30-2 may be similar to the system 30-1 illustrated in FIG. 3B except that, for example, the second scanner 32-2 is employed. Specifically, the first scanner 32-1 and the second scanner 32-2 may be disposed at one side of the product 31, while the first light source 37-1 may be disposed at the other side the product 31. Moreover, the first scanner 32-1 may be disposed at a first distance $d_1$ from the product 31 and the second scanner 32-2 may be disposed at a second distance $d_2$ from the product 31 so that a specific layer of the product 31 where a defect exists may be identified.

Figure 3D:
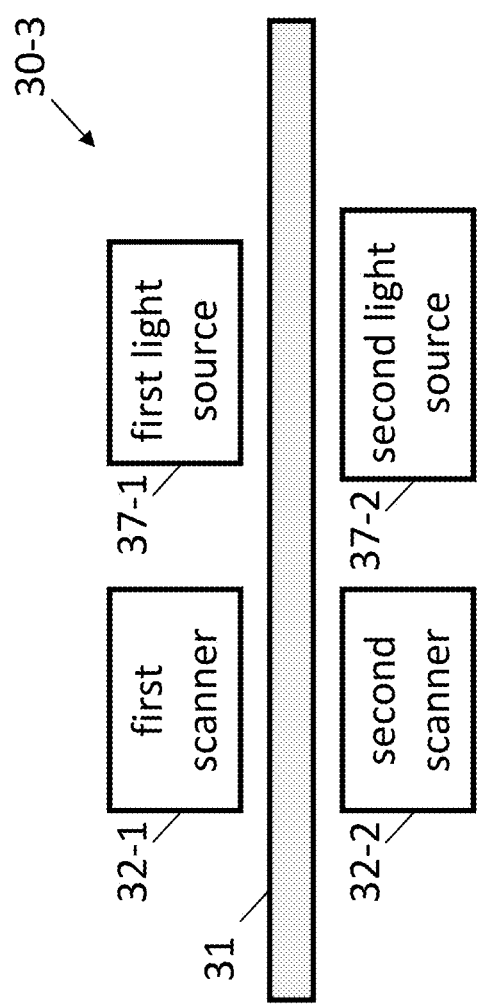
FIG. 3D is a schematic diagram of a system for inspection in accordance with yet still another example of the present invention.

FIG. 3D is a schematic diagram of system 30-3 for inspection in accordance with yet still another example of the present invention. Referring to FIG. 3D, the first scanner 32-1 and the first light source 37-1 may be disposed at one side of the product, while the second scanner 32-2 and a second light source 37-2 may be disposed at the other side of the product 31. The product 31 in the present example may include multiple layers that may further include a first layer (not shown), a second layer (not shown) and at least one intermediate layer between the first and second layers. The at least one intermediate layer may be an optically opaque layer, which may include device features such as conductive lines and circuit components. With the arrangement, the first and second layers of the multi-layer product 31 may be scanned at the same time.

Figure 4:
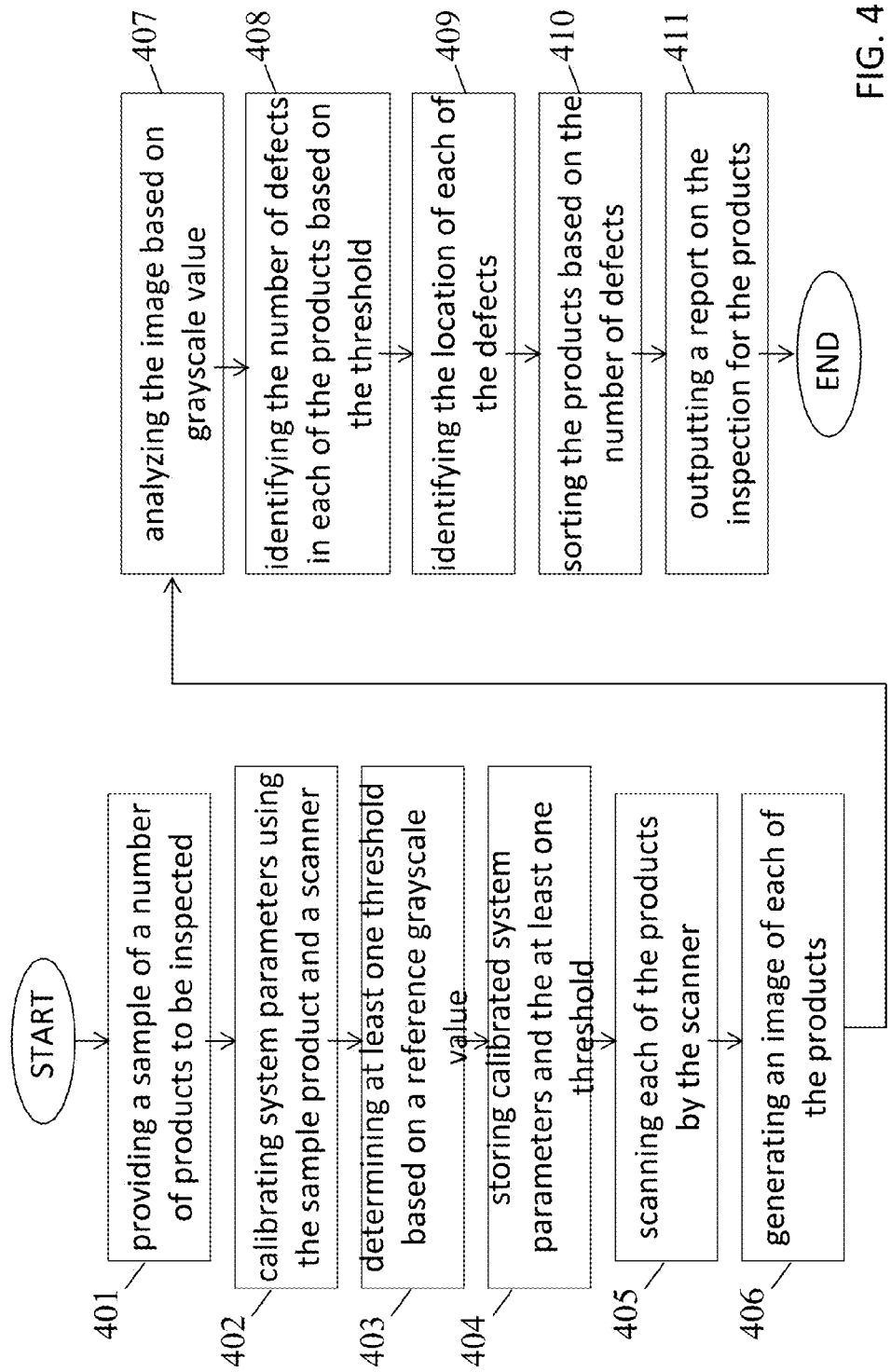
FIG. 4 is a flow diagram illustrating a method of inspection in accordance with an example of the present invention.

FIG. 4 is a flow diagram illustrating a method of inspection in accordance with an example of the present invention. Referring to FIG. 4, at step 401, a sample of a number of products to be inspected may be provided.

At step 402, system parameters such as display pattern, the sensitivity of a scanner and the distance between the scanner and the sample product may be calibrated by scanning the sample product. In calibrating the sensitivity of the scanner, a reference grayscale value for each of pixels in a scanned image of the sample product may be obtained. The reference grayscale value may refer to an evenly averaged or a weighted average or the grayscale values of pixels in the neighborhood of the each pixel.

At step 403, at least one threshold based on the reference grayscale value for each of the pixels may be determined in order for the detection of defects in the products during the inspection. The at least one threshold in one example may include a first threshold for the detection of bright dots and a second threshold for the detection of dark dots.

Next, at step 404, calibrated data and the at least one threshold for each of the pixels may be stored so as to facilitate the inspection of the products. Steps 401 to 404 may collectively refer to an initialization or calibration process.

Each of the products may then be scanned by a scanner one after another at step 405.

At step 406, the scanner may generate an image of the each of the products. The image may include a matrix of pixels each having a grayscale value.

The image may be analyzed at step 407 by comparing each of the pixels of the image with the at least one threshold associated with the each pixel.

At step 408, if the grayscale value of a pixel is greater than the upper limit or smaller than the lower limit of the at least one threshold, the pixel is recognized as a defected pixel. The number of defects in each of the products may be calculated.

Since the pixels are arranged in a matrix, at step 409, the location or coordinates of each of the defects, if any, may be identified.

Next, at step 410, the products may be sorted by the number of defects.

Subsequently, a report on the number of defects in each of the products, the grade or quality of each of the products and the location of each of the defects may be provided at step 411.

Figure 5:
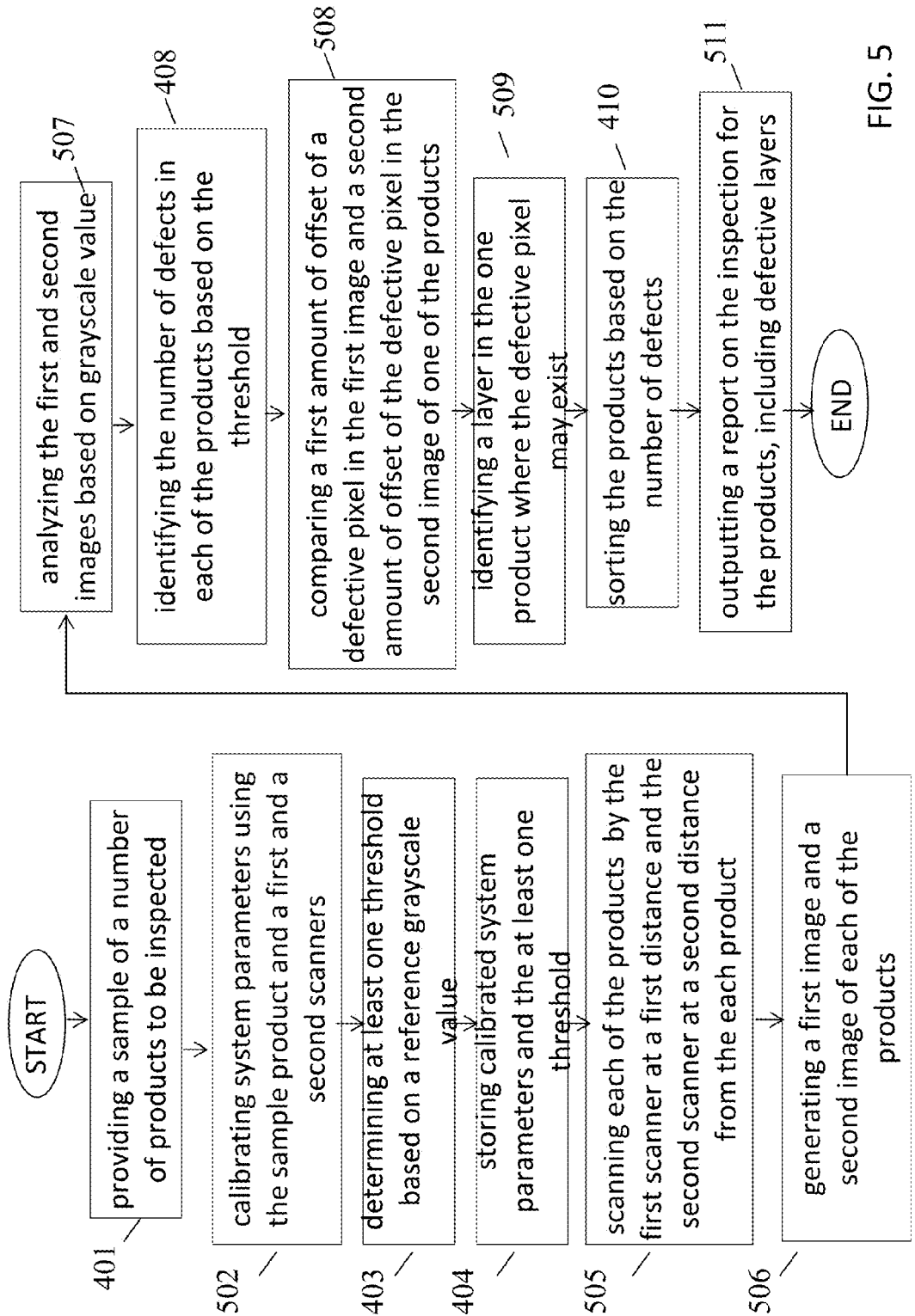
FIG. 5 is a flow diagram illustrating a method of inspection in accordance with another example of the present invention.

FIG. 5 is a flow diagram illustrating a method of inspection in accordance with another example of the present invention. Referring to FIG. 5, the method may be similar to that described and illustrated with reference to FIG. 4 except that, for example, two scanners may be employed.

Specifically, at step 502, a first scanner and a second scanner may be used in the calibration stage.

Subsequently, at step 505, a product under inspection may be scanned by the first scanner and the second scanner disposed at a first distance and a second distance from the product, respectively. The first distance may be associated with a first layer of interest in the product and the second distance may be associated with a second layer of interest in the product.

Accordingly, at step 506, a first image of the product may be generated by the first scanner and a second image of the product may be generated by the second scanner.

Next, the first image and the second image of the product may be analyzed at step 507 based on the threshold. The number of defects, if any, in each of the products may be identified at step 408.

At step 508, a first amount of offset of a defective pixel in the first image and a second amount of offset of the defective pixel in the second image of one of the products with defects may be compared so as to determine which layer in the product the defective pixel is located at step 509.

Subsequently, at step 511, a report on the number of defects in each of the products, the grade or quality of each of the products and the layer of the product where a defect exists may be provided.

It will be appreciated by those skilled in the art that changes could be made to the examples described above without departing from the broad inventive concept thereof. It is understood, therefore, that this invention is not limited to the particular examples disclosed, but it is intended to cover modifications within the spirit and scope of the present invention as defined by the appended claims.

Further, in describing representative examples of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

We claim:

1. A system for inspecting a product, the system comprising:
    a scanner including at least one scanning unit arranged in a first direction that is sufficient to cover a width of a scanning area of the system in the first direction and configured to scan across the product and generate an image of the product, the image including a matrix of pixels each having a grayscale value; and
    an analyzing device electrically coupled with the scanner to receive and analyze the image of the product, the analyzing device including:
        a microprocessor to calculate a reference grayscale value associated with each of the pixels in the image, wherein the reference grayscale value includes an average of the grayscale values of pixels located adjacent to the each pixel;
        a memory to store the reference grayscale value associated with each of the pixels and at least one threshold associated with the reference grayscale value; and
        a comparing module to compare the grayscale value of each of the pixels in the image with the at least one threshold associated with the each pixel.

2. The system of claim 1, wherein the scanner is configured to move with respect to the product in a second direction orthogonal to the first direction.

3. The system of claim 2, wherein the scanner includes a first column of scanning units and a second column of scanning units, the first and second columns of scanning units configured to be staggered with respect to each other.

4. The system of claim 3, wherein each of the scanning units includes a number of sensor cells, and a scanning unit in the first column overlaps an immediately adjacent scanning unit in the second column by a predetermined number of sensor cells.

5. The system of claim 3, wherein each of the scanning units includes a number of sensor cells, and wherein the density of scanning units in the each scanning unit is equal to or greater than twice the density of sub-pixels in the product.

6. The system of claim 1 further comprising a sorting module to sort a number of the products by the number of defects.

7. The system of claim 1, wherein the at least one threshold includes a first threshold that is an upper limit of the reference grayscale value and a second threshold that is a lower limit of the reference grayscale value.

8. The system of claim 1, wherein the scanner is a first scanner to scan a first layer of the product and generate a first image, further comprising a second scanner to scan a second layer of the product and generate a second image.

9. The system of claim 8, wherein the comparing module is configured to compare a first amount of offset from the at least one threshold associated with a pixel in the first image with a second amount of offset from the at least one threshold associated with the pixel in the second image.

10. A system for inspecting a product, the system comprising:
    a scanner including at least one scanning unit arranged in a first direction that is sufficient to cover a width of a scanning area of the system in the first direction and configured to scan across the product in a second direction orthogonal to the first direction, the scanner generating an image of the product, the image including a matrix of pixels each having a grayscale value;
    a microprocessor to calculate a reference grayscale value associated with each of the pixels in the image, wherein the reference grayscale value includes an average of the grayscale values of pixels located adjacent to the each pixel; and
    a comparing module to compare the grayscale value of each of the pixels in the image with a first threshold and a second threshold associated with the each pixel, wherein the first threshold includes an upper limit of the reference grayscale value and the second threshold includes a lower limit of the reference grayscale value.

11. The system of claim 10 further comprising a memory to store the reference grayscale value associated with each of the pixels and the first and second thresholds associated with the reference grayscale value.

12. The system of claim 10, wherein the scanner includes a first column of scanning units and a second column of scanning units, the first and second columns of scanning units being staggered with respect to each other.

13. The system of claim 12, wherein each of the scanning units includes a number of sensor cells, and a scanning unit in the first column overlaps an immediately adjacent scanning unit in the second column by a predetermined number of sensor cells.

14. The system of claim 12, wherein each of the scanning units includes a number of sensor cells, and wherein the density of scanning units in the each scanning unit is equal to or greater than twice the density of sub-pixels in the product.

15. The system of claim 10 further comprising a sorting module to sort a number of the products by the number of defects.

16. A system for inspecting a product, the system comprising:
    a first scanner including at least one scanning unit arranged in a first direction that is sufficient to cover a width of a scanning area of the system in the first direction and configured to scan across the product and generate a first image of the product, the first image including a matrix of pixels each having a grayscale value;
    a second scanner including at least one scanning unit arranged in the first direction that is sufficient to cover the width of the scanning area of the system in the first direction and configured to scan across the product and generate a second image of the product, the second image including a matrix of pixels each having a grayscale value; and
    an analyzing device electrically coupled with the first scanner and the second scanner to receive and analyze the first and second images of the product, the analyzing device including:
        a microprocessor to calculate a reference grayscale value associated with each of the pixels in the first and second images, wherein the reference grayscale value includes an average of the grayscale values of pixels located adjacent to the each pixel;
        a memory to store the reference grayscale value associated with each of the pixels in the first and second images and at least one threshold associated with the reference grayscale value; and
        a comparing module to compare the grayscale value of each of the pixels in the first and second images with the at least one threshold associated with the each pixel.

17. The system of claim 16, wherein the first scanner and the second scanner are configured to move with respect to the product in a second direction orthogonal to the first direction.

18. The system of claim 17, wherein both the first scanner and the second scanner include a first column of scanning units and a second column of scanning units, the first and second columns of scanning units being staggered with respect to each other.

19. The system of claim 16, wherein the at least one threshold includes a first threshold that is an upper limit of the reference grayscale value and a second threshold that is a lower limit of the reference grayscale value.

20. The system of claim 16, wherein the comparing module is configured to compare a first amount of offset from the at least one threshold associated with a pixel in the first image with a second amount of offset from the at least one threshold associated with the pixel in the second image.

* * * * *